United States Patent
Sloman et al.

(10) Patent No.: US 6,587,723 B1
(45) Date of Patent: Jul. 1, 2003

(54) METHOD AND SYSTEM FOR AUTOMATICALLY MEASURING CAPTURE THRESHOLD IN AN IMPLANTABLE CARDIAC STIMULATION DEVICE

(75) Inventors: Laurence S. Sloman, West Hollywood, CA (US); Kerry A. Bradley, Glendale, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 193 days.

(21) Appl. No.: 09/690,565

(22) Filed: Oct. 17, 2000

(51) Int. Cl.$^7$ ............................................. A61N 1/368
(52) U.S. Cl. ..................................................... 607/28
(58) Field of Search ............................ 600/509; 607/4, 607/5, 9, 11, 27, 28

(56) References Cited

U.S. PATENT DOCUMENTS

| | | | |
|---|---|---|---|
| 4,686,988 A | 8/1987 | Sholder | 128/419 PT |
| 4,766,901 A | 8/1988 | Callaghan | 128/419 PG |
| 4,955,376 A | 9/1990 | Callaghan et al. | 128/419 PG |
| 4,969,462 A * | 11/1990 | Callaghan et al. | 128/419 PG |
| 4,969,467 A | 11/1990 | Callaghan et al. | 128/419 PG |
| 5,350,410 A | 9/1994 | Kleks et al. | 607/28 |
| 5,466,254 A | 11/1995 | Helland | 607/123 |
| 5,534,016 A * | 7/1996 | Boute | 607/9 |
| 5,861,012 A | 1/1999 | Stroebel | 607/28 |
| 5,891,178 A * | 4/1999 | Mann et al. | 607/27 |
| 6,038,474 A * | 3/2000 | Zhu et al. | 607/9 |
| 6,311,089 B1 * | 10/2001 | Mann et al. | 607/30 |
| 6,366,812 B1 * | 4/2002 | Levine et al. | 607/27 |
| 6,427,085 B1 * | 7/2002 | Boon et al. | 607/28 |

OTHER PUBLICATIONS

Sylven, J. et al., Pacing Threshold Interval with Decreasing and Increasing Output, *PACE*, vol. 5, pp 646–649, (Sep.–Oct. 1982).

* cited by examiner

Primary Examiner—Jeffrey R. Jastrzab
Assistant Examiner—Frances P. Oropeza

(57) ABSTRACT

An implantable cardiac stimulation device with automatic threshold testing capabilities. The device utilizes an algorithm for measuring a first and a second threshold settings. The first threshold setting is determined by decreasing the stimulation energy from an initially high, supra-threshold value until loss of capture is detected, and is set as the pulse energy at which capture is still detected. The second threshold setting is determined by increasing the stimulation energy from an initially low, sub-threshold value until capture is detected, and is set as the stimulation energy at which capture is regained. The algorithm further determines if the threshold test results are reliable by comparing the difference between the first and second threshold settings to an expected difference, known as the Wedensky Effect value. A deviation from the Wedensky Effect value which is known for a given patient, indicates a discrepancy in the threshold test result. Such a deviation could be used to indicate when a threshold test is suspected of being erroneous, for example, due to fusion. During a subsequent threshold test, the stimulation parameters are adjusted so that the likelihood of fusion is minimized. Once a threshold test result is evaluated and found to be consistent with the expected Wedensky Effect value, the stimulation energy is automatically adjusted to a level safely above the threshold value.

22 Claims, 6 Drawing Sheets

METHOD AND SYSTEM FOR AUTOMATICALLY MEASURING CAPTURE THRESHOLD IN AN IMPLANTABLE CARDIAC STIMULATION DEVICE

FIELD OF THE INVENTION

This invention relates generally to an implantable cardiac stimulation system capable of automatically performing threshold tests, and more specifically, to a method for verifying that the result of a given threshold test is not due to fusion activity.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions. Disruption of this natural pacemaking and conduction system as a result of aging or disease can be successfully treated by artificial cardiac pacing using implantable cardiac pacing devices, including pacemakers and implantable defibrillators, which deliver rhythmic electrical pulses or other anti-arrhythmia therapies to the heart at a desired energy and rate. One or more heart chambers may be electrically stimulated depending on the location and severity of the conduction disorder.

Modern pacemakers and implantable defibrillators possess numerous operating parameters, such as pacing pulse energy, base pacing rate, sensing threshold, pacing mode, etc., that must be programmed by the physician to satisfy individual patient need. In practice, this programming process can be time consuming and complicated. A common goal of pacemaker manufacturers, therefore, is to fully automate pacemaker function in order to minimize the complexity of programming operations and to maximize the safety and effectiveness of the cardiac pacing device.

One function of the cardiac stimulating device is therefore to deliver a stimulation pulse of sufficient energy to depolarize the cardiac tissue causing a contraction, a condition commonly known as "capture." One approach to ensure capture is to deliver a fixed high-energy pacing pulse. While this approach, used in early pacemakers, is straightforward, it quickly depletes battery energy and can result in patient discomfort due to extraneous stimulation of surrounding skeletal muscle tissue.

Preferably, stimulation pulses are delivered at, or slightly higher than the capture "threshold." Capture threshold is defined as the lowest stimulation energy at which capture occurs. By stimulating the heart chambers at, or just above threshold, comfortable and effective cardiac pacing is provided without unnecessary depletion of battery energy. Capture threshold, however, is extremely variable from patient-to-patient due to variations in electrode systems used, electrode positioning, physiological and anatomical variations of the heart itself, and so on. Therefore, at the time of device implant, the capture threshold is determined by the physician who observes an ECG recording while pulse energy is decreased starting from a high level, either by decrementing the pulse amplitude or the pulse width, until capture disappears.

The pacing pulse energy is then programmed to a setting equal to the lowest pulse energy at which capture still occurred (threshold) plus some safety margin to allow for small fluctuations in threshold. Selection of this safety margin, however, can be arbitrary. Too low of a safety margin may result in loss of capture, with a potentially fatal result for the patient. Too high of a safety margin will lead to premature battery depletion and potential patient discomfort.

Furthermore, pacing threshold will vary over time within a patient, for example, as fibrotic encapsulation of the electrode occurs during the first few weeks after surgery. Fluctuations may even occur over the course of a day or with changes in medical therapy or disease state. Hence, techniques for monitoring the cardiac activity following delivery of a stimulation pulse have been incorporated in modem pacemakers in order to verify that capture has indeed occurred. If a loss of capture is detected by such "capture-verification" algorithms, a threshold test is performed by the cardiac stimulating device in order to re-determine the capture threshold and automatically adjust the stimulation pulse energy. This approach, called "autocapture", improves the patient's comfort, reduces the necessity of unscheduled visits to the medical practitioner, and greatly increases the device battery life by conserving the energy used to generate stimulation pulses.

One technique for determining whether capture has occurred is monitoring the myocardial electrogram (EGM) received on the cardiac pacing and sensing electrodes. Heart activity is monitored by the cardiac stimulation device by keeping track of the stimulation pulses delivered to the heart and examining the EGM signals for evidence of depolarization or contraction of muscle tissue (myocardial tissue) of the heart immediately following stimulation delivery. Through sampling and signal processing algorithms, the presence of an "evoked response", either an intracardiac P-wave or R-wave, following a pacing pulse can be determined. The "evoked response" is the depolarization of the heart tissue in response to a pacing pulse, in contrast to the "intrinsic response" which is the depolarization of the heart tissue in response to the heart's natural pacemaking function. Detection of an evoked response indicates capture was achieved.

However, it is for several reasons very difficult to detect a true evoked response. One problem commonly encountered during capture verification is "fusion." Fusion occurs when a pacing pulse is delivered such that the evoked response occurs coincidentally with an intrinsic depolarization. The evoked signal may be absent or altered preventing correct capture detection by the pacemaker's capture detection algorithm. A loss of capture may be indicated when capture is in fact present, an undesirable situation that will cause the pacemaker to unnecessarily deliver a high-energy back-up pacing pulse, and to invoke the threshold testing function in a chamber of the heart.

An even more adverse affect of fusion is when fusion occurs during a threshold test causing an erroneously high threshold result. Automatic adjustment of the pacing pulse energy to this higher output will waste battery energy until the next threshold test is initiated. In extreme situations, fusion could persist throughout a threshold test, driving the pacing energy output to a maximum level.

A common practice in minimizing the likelihood of fusion during a threshold test is temporarily changing stimulation parameters, e.g. base pacing rate and/or the atrio-ventricular delay. Increasing the pacing rate a given level above the sensed rate during the threshold test decreases the likelihood that the pacing pulse will be delivered coincidentally with an intrinsic response. During dual chamber pacing, the atrio-ventricular (AV) delay can be shortened such that pacing in the ventricle will safely occur earlier than the anticipated intrinsic ventricular response. However, while changing stimulation parameters may lessen the chance of fusion occurring during a threshold test, it does not guarantee that fusion will not occur.

One method of performing a threshold test is to start at a pacing pulse energy at which capture is already occurring, i.e. supra-threshold, and progressively decrement pulse energy until capture is lost. The lowest pulse energy at which capture is maintained is deemed the threshold value. Another method of performing a threshold test is to start at a sub-threshold pulse energy and progressively increment pulse energy until capture is achieved. Again, the lowest pulse energy at which capture is maintained is considered the threshold value.

These two methods, however, will consistently arrive at different threshold results, even in the same patient under the same set of circumstances, due to a phenomenon known as the "Wedensky Effect." The threshold result from the first technique of progressively decrementing pulse energy from a supra-threshold level will provide a lower threshold result than the second technique of starting from a sub-threshold level and progressively incrementing pulse energy. This phenomenon can best be described as a facilitating effect of electrically excitable tissue. Once excitable tissue has already been depolarized by an electrical impulse, less energy is required to continue exciting the tissue then the energy that was required to initially depolarize the tissue from an unexcited state. This effect is also referred to as "threshold hysteresis."

Clinical studies of patients having implanted cardiac stimulating devices have found that the difference between the two threshold results, hereafter referred to as the Wedensky Effect value, is constant regardless of the actual threshold levels, the duration of device implant, disease state, or intrinsic cardiac activity (reference is made to "Pacing Threshold Interval with Decreasing and Increasing Output," Sylven et al, PACE, 5:646–9, 1982).

It would thus be desirable to provide a system and method for reliably and accurately determining capture threshold. It would further be desirable to determine when a threshold measurement is likely to have been affected by fusion. Furthermore, when a threshold result is suspected of being erroneous due to fusion, it is desirable to re-determine threshold by performing a new threshold test under conditions that minimize the likelihood of fusion. By reliably and accurately determining pacing threshold, battery energy is conserved, improving overall device performance.

SUMMARY OF THE INVENTION

The present invention addresses these and other concerns by providing an implantable cardiac stimulation device with automatic threshold testing capabilities. One aspect of the present invention is to provide a method for measuring a first threshold and a second threshold. The first threshold is determined by decreasing stimulation energy from an initially high, supra-threshold value until loss of capture is detected. The pulse energy at which capture is lost is the first threshold value. The second threshold value is determined by increasing the stimulation energy from an initially low, sub-threshold value until capture is detected. The stimulation energy at which capture is regained is the second threshold value.

Another aspect of the present invention is to provide a method for determining if the threshold test results are reliable, by comparing the difference between the first and second threshold values to an expected difference, known as the Wedensky Effect, for a particular patient. Therefore, one feature of the present invention is the automatic determination of the expected Wedensky Effect for the particular patient by calculating a mean Wedensky Effect and its standard deviation based on all previous threshold tests performed on that patient. A deviation from the Wedensky Effect value known for a given patient indicates a discrepancy in the threshold test result. Such a deviation is used to indicate when a threshold test is suspected of being erroneous, for example, due to fusion. For example, if the difference between the first threshold value and the second threshold value is a given amount greater than the mean Wedensky Effect value, the threshold test is suspected of being erroneous due to fusion occurring during the threshold test.

A further aspect of the present invention is a method for redetermining threshold when a threshold test result is suspected of being erroneous due to fusion. During a second threshold test, stimulation parameters are adjusted so that the likelihood of fusion is minimized. Once a threshold test result is evaluated and found to be consistent with the expected Wedensky Effect value, the stimulation energy is automatically adjusted to a level safely above the threshold value.

Thus, the present invention teaches a cardiac stimulating device and electrode system capable of delivering stimulating pulses to a given heart chamber and detecting when capture occurs. The present invention further includes a method for automatic threshold testing. The associated method of the present invention determines whether fusion may have interfered with obtaining accurate threshold test results, and automatically adjusts the stimulation energy based on the threshold test results once they have been verified as being reliable. This automatic adjustment of stimulation energy maintains the minimum energy necessary for effective stimulation therapy delivery thus improving battery longevity.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated above, the present invention is directed primarily at providing automatic threshold testing in an implantable cardiac stimulating device, including single-chamber, dual-chamber or multi-chamber stimulating devices. One embodiment of a multi-chamber cardiac stimulation device possessing pacemaking, cardioversion and/or defibrillation capabilities, in which threshold testing according to the present invention could be implemented, is described in conjunction with FIGS. 1 and 2. It is recognized, however, that numerous variations of such a device exist in which the methods to be described herein could be implemented without deviating from the scope of the present invention.

Figure 1:
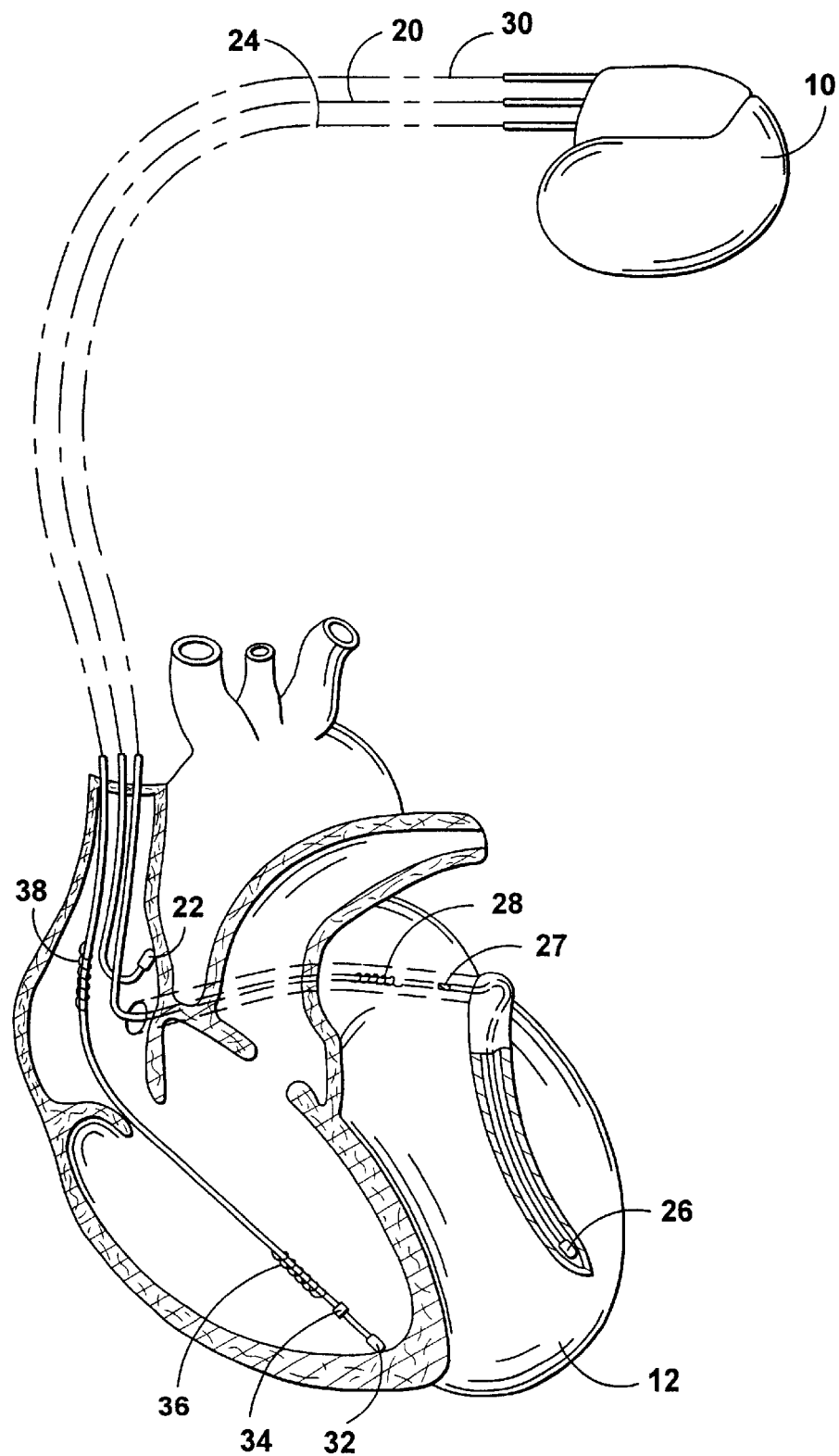
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os, so as to place a distal electrode adjacent to the left ventricle and additional electrode(s) adjacent to the left atrium. As used herein, the term "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using at least a left ventricular tip electrode 26, left atrial pacing therapy using at least a left atrial ring electrode 27, and shocking therapy using at least a left atrial coil electrode 28. For a more detailed description of a coronary sinus lead, refer to U.S. patent application Ser. No. 09/457,277, titled "A Self-Anchoring, Steerable Coronary Sinus Lead" (Pianca et al.), and U.S. Pat. No. 5,466,254, titled "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
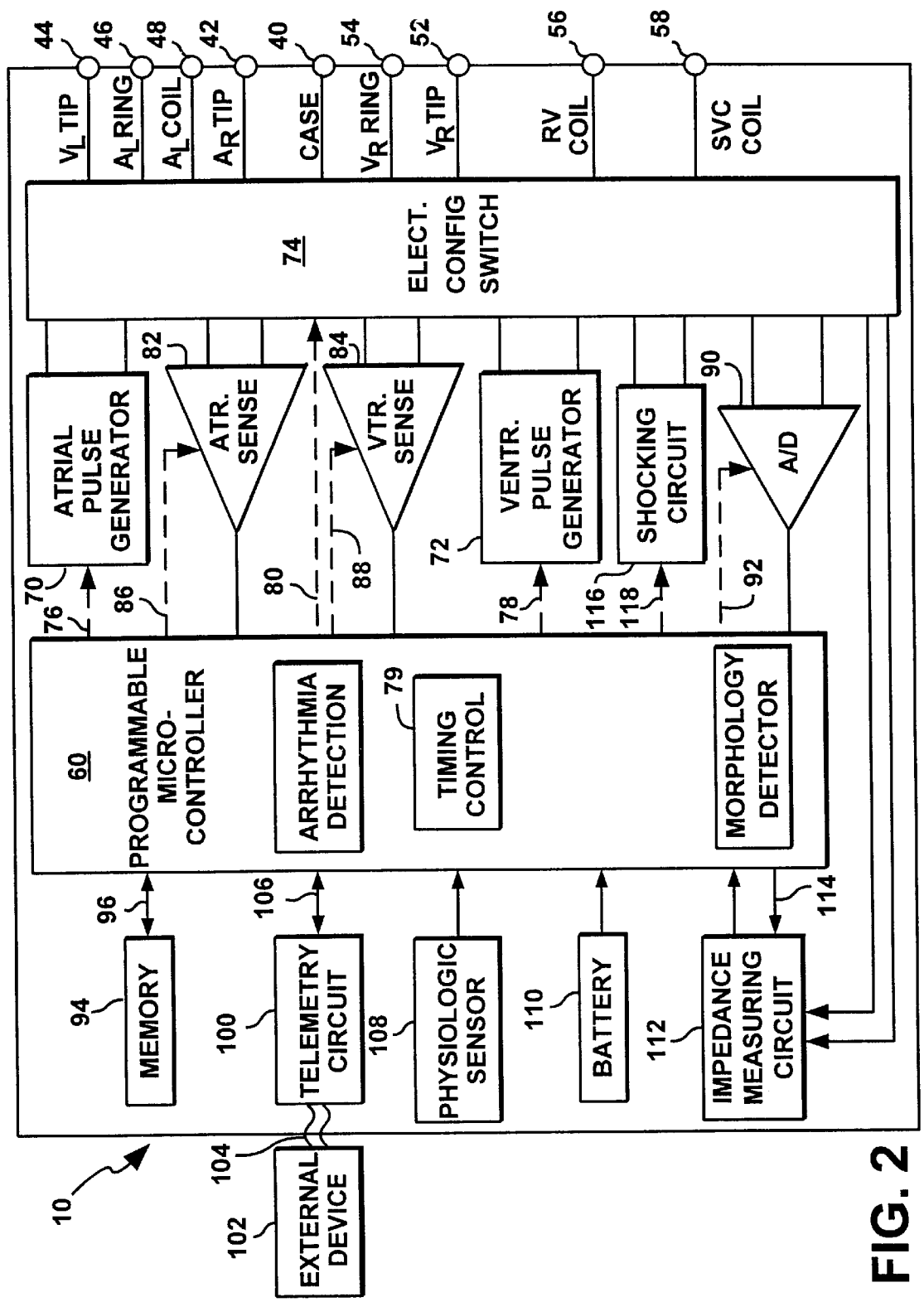
FIG. 2 is a functional block diagram of the multi-chamber implantable stimulation device of FIG. 1, illustrating the basic elements that provide cardioversion, defibrillation and/or pacing stimulation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal 42 adapted for connection to the atrial (AR) tip electrode 22.

To achieve left chamber sensing, pacing and/or shocking, the connector includes at least a left ventricular ($V_L$) tip terminal 44, a left atrial ($A_L$) ring terminal 46, and a left atrial ($A_L$) shocking terminal 48, which are adapted for connection to the left ventricular tip electrode 26, the left atrial tip electrode 27, and the left atrial coil electrode 28, respectively.

To support right chamber sensing, pacing and/or shocking, the connector further includes a right ventricular ($V_R$) tip terminal 52, a right ventricular ($V_R$) ring terminal 54, a right ventricular (RV) shocking terminal 56, and an SVC shocking terminal 58, which are adapted for connection to the right ventricular tip electrode 32, the right ventricular ring electrode 34, the RV coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial interconduction (A—A) delay, or ventricular interconduction (V—V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred.

Capture detection may occur on a beat-by-beat basis or on a sampled basis. Whenever loss of capture is detected, a threshold test is automatically performed. A threshold test may also be initiated by an external command given by the programmer, or by microprocessor 60 based on an event-triggered or pre-determined periodic basis. In one embodiment, a threshold test is performed once a day during at least the acute phase (e.g. the first 30 days) and less frequently thereafter.

In accordance with the present invention, a threshold test is performed by first decreasing the stimulating energy until capture is lost. The energy at which capture was lost is stored in memory 94. The first threshold test is immediately followed by a second threshold test performed by starting from the subthreshold stimulating energy at which the first threshold test ended. Stimulating energy is then progressively increased until capture is just regained, giving a second threshold value. This second threshold value is also stored in memory 94. The difference between the first threshold value and the second threshold value is calculated. This difference, herein referred to as the Wedensky Effect value, is expected to remain constant regardless of actual threshold levels, implant duration, or patient condition as long as fusion does not interfere during the threshold test. The Wedensky Effect value is thus used to determine if the threshold test results are reliable by comparing it to the mean Wedensky Effect value determined from all previous threshold tests performed in the same patient.

Figure 3:
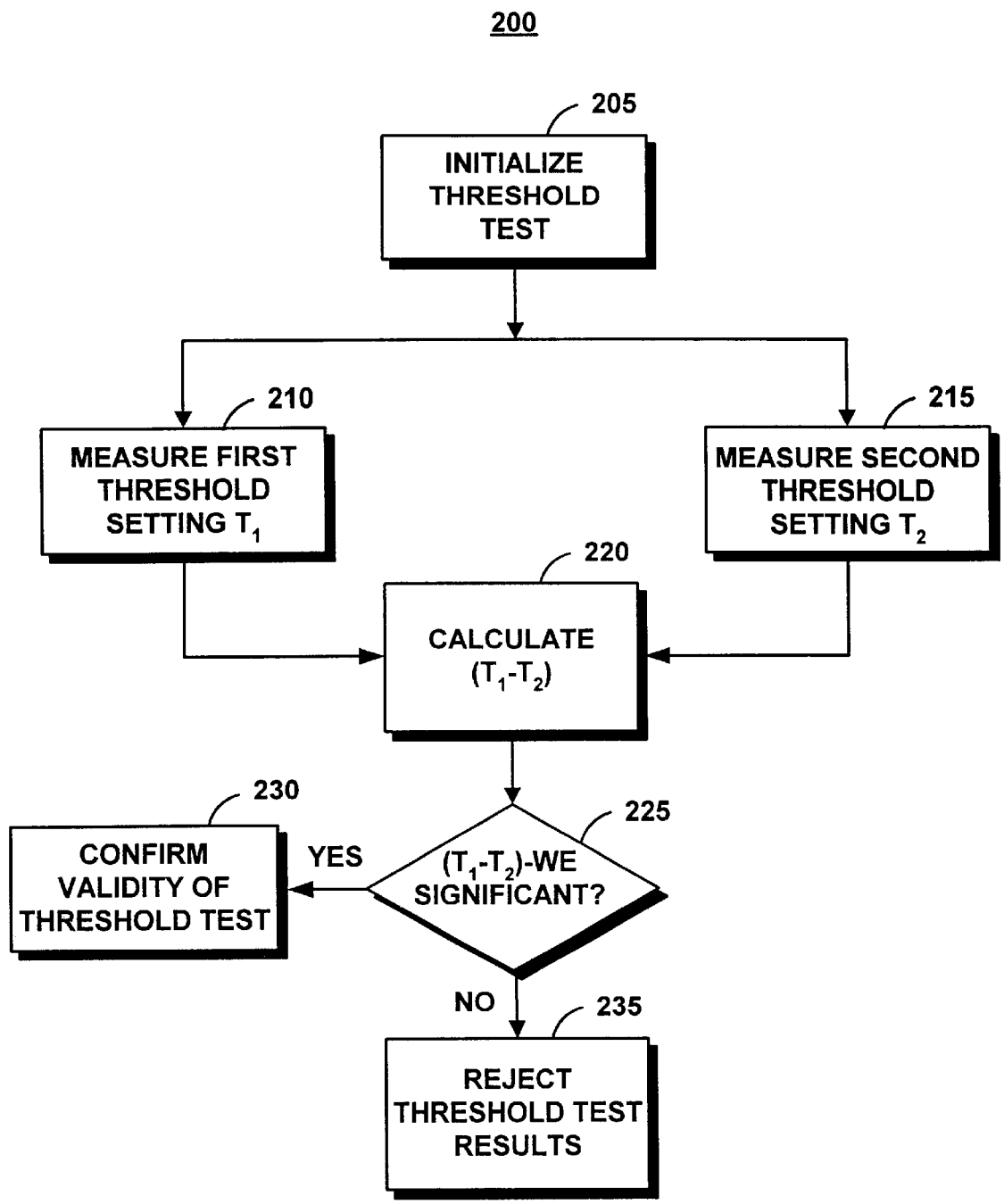
FIG. 3 is a high level functional flow chart illustrating an overview of the operation of the stimulation device of FIG. 2.

FIG. 3 illustrates a high level architecture of a method 200 for automatically performing the threshold test of the present invention. The threshold test is first initiated at step 205. The stimulation device 10 measures the first threshold setting ($T_1$) at step 210 by progressively decreasing the stimulation pulse energy until capture is lost, and further measures the second threshold setting ($T_2$) at step 215 by progressively increasing the stimulation pulse energy until capture is verified. The stimulation device 10 then calculates the difference between the first and second threshold settings ($T_1$) and ($T_2$) at step 220, and further calculates the deviation of this difference from the Wedensky Effect value (WE) at step 225. If such deviation is significant, the stimulation device 10 confirms the validity of the threshold test at step 230; otherwise, it rejects the threshold test result at step 235. A more detailed description of the method 200 used in performing a threshold test and verifying that the threshold test result is erroneous due to fusion will be described later in conjunction with FIGS. 4 and 5.

It is recognized that various capture detection methods may be used successfully in the threshold testing methods of the present invention. For a more detailed description of the implementation of capture detection circuitry and algorithms refer, for example, to U.S. Pat. No. 4,686,988 (Sholder); U.S. Pat. No. 4,969,467 (Callaghan et. al, and U.S. Pat. No. 5,350,410 (Klecks et. al), which patents are hereby incorporated herein by reference.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

A feature of the present invention is the ability to sense and store a relatively large amount of data (e.g. from the data acquisition system 90), which data may then be used for subsequent analysis to guide the programming of the stimulation device 10. In accordance with a preferred embodiment, all threshold test data is stored in memory 94 to be used in determining whether the result of a new threshold test is anomalous.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In one embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diumal changes in activity (e.g. detecting sleep and wake states). Accordingly, the microcontroller 60 responds by adjusting the various stimulation parameters (such as rate, AV Delay, V—V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, and also be capable of providing high-current pulses (for capacitor charging) when the patient requires a shock pulse. The battery 110 preferably has a predictable discharge characteristic so that elective replacement time can be detected. Accordingly, the stimulation device 10 can employ lithium/silver vanadium oxide batteries.

As further shown in FIG. 2, the stimulation device 10 is shown as having an impedance measuring circuit 112 which is enabled by the microcontroller 60 by a control signal 114. The known uses for an impedance measuring circuit 120 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of the valves, etc. The impedance measuring circuit 120 is advantageously coupled to the switch bank 74 so that any desired electrode may be used.

In the case where the stimulation device 10 is intended to operate as an implantable cardioverter/defibrillator (ICD) device, it needs to detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 4A:
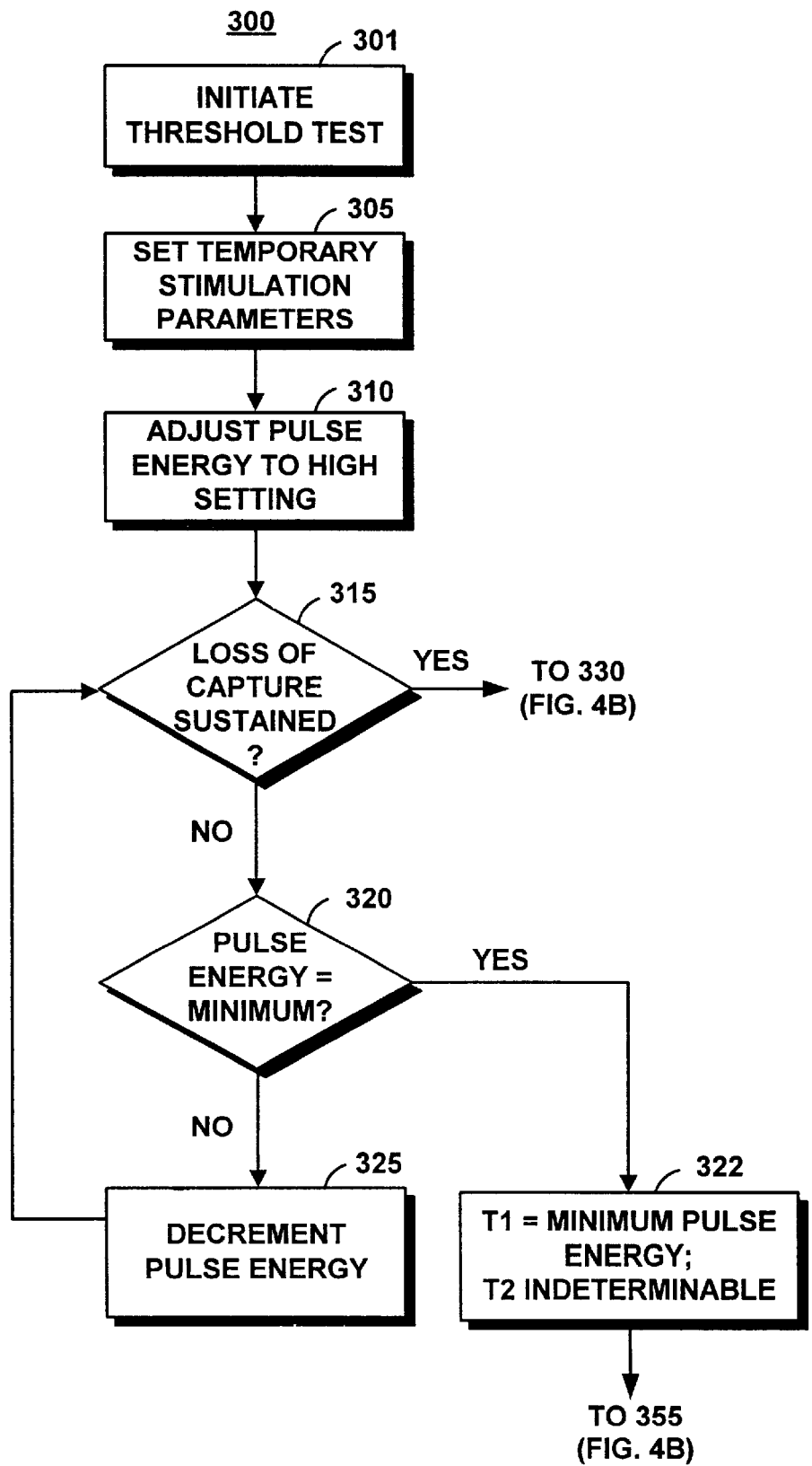
FIG. 4 is comprised of FIGS. 4A and 4B, and represents a more detailed flow chart illustrating the operation of the stimulation device of FIG. 3, in which a threshold test is performed.

FIG. 4 illustrates a flow chart that describes an overview of the operation and features implemented in one embodiment of the stimulation device 10 for performing a threshold search. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

A threshold test method or algorithm 300 shown in FIG. 4 is initiated at step 301. As described earlier, the threshold test method 300 may be initiated upon a loss of capture detection during autocapture or other capture verification routines, or it may be initiated by an externally generated command or by a command from the microprocessor 60.

Once initiated, the method 300 adjusts the stimulation parameters at step 305 to predefined temporary settings that will induce stable stimulation, allowing a threshold test to be performed. Stimulation parameters may be adjusted by increasing the base stimulation rate to a given rate above the sensed rate, for example 10 beats per minute above the sensed rate. Additionally or alternatively, the atrial-ventricular stimulation interval may be shortened by a defined interval, for example 50 msec shorter than the programmed interval. Increasing the base stimulation rate and/or shortening the atrial-ventricular stimulation interval advantageously causes the stimulation device 10 to predominate over the natural heart rhythm, allowing the threshold test method 300 to be performed.

The stimulating pulse energy is then increased to an initially higher setting expected to ensure capture at step 310. The pulse energy is increased by increasing either the pulse amplitude, the pulse width, or both. The initial setting may be a fixed or programmable value stored in memory 94, such as the maximum pulse amplitude available. Alternatively, this initial setting may be defined by a relationship to the currently programmed pulse energy, for example two times the presently programmed pulse amplitude. If the threshold test method 300 has been initiated due to a detected loss of capture, the adjustment is preferably a very high setting in order to ensure capture, such as the maximum pulse amplitude or twice the measured threshold. If the threshold test is initiated by an external or microprocessor-generated command, the pulse energy is preferably adjusted to the last setting at which capture is known to have occurred.

At decision step 315, the method 300 determines if loss of capture has occurred for a defined number of consecutive stimulation cycles (n) in which new pulse energy has been delivered. The number of consecutive cycles (n) may be predefined and stored in memory or it may be a programmable value, typically on the order of one to five consecutive cycles, but preferably two consecutive cycles. Capture is verified by sensing the EGM signal of the paced chamber in order to detect an evoked response. Capture may also be verified using other techniques such as sensing for a conducted response in another chamber following capture in the paced chamber, or detection of the heart chamber contraction using other sensed signals such as piezoelectric sensors, blood pressure sensors, blood velocity sensors, and so on.

Since the initial pulse energy is expected to ensure capture, the method 300 determines at step 315 whether capture has been effected, and proceeds to step 320 where a determination is made as to whether the pulse energy is at the minimum setting available. Since the initial pulse energy is a high setting, the answer to the inquiry at step 320 is most probably negative, and the method 300 proceeds to step 325.

At step 325, the method 300 decreases the stimulation energy by reducing the pulse amplitude or the pulse width by a defined step. Various algorithms by which the stimulating pulse energy can be progressively decreased may be implemented successfully within the scope of the present invention.

Figure 4B:
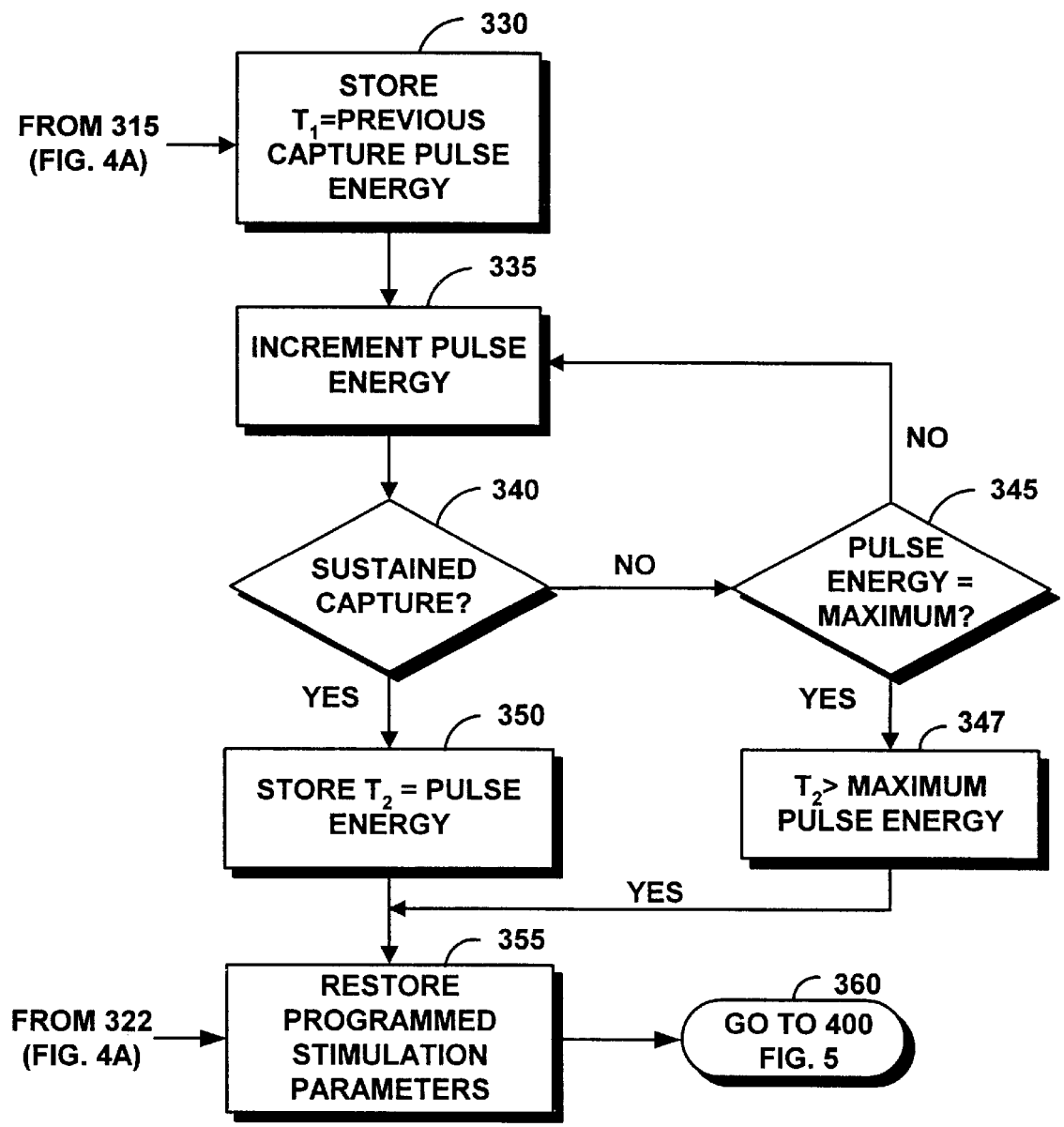

Next, the method 300 returns to decision step 315 to determine if a sustained loss of capture is verified for n consecutive stimulation cycles. If not, steps 315, 320 and 325 are repeated until sustained loss of capture is verified at step 315. The pulse energy setting at which sustained loss of capture is detected is considered to be the subthreshold setting. This pulse energy setting is considered to be the threshold setting $T_1$ and is stored in memory 94 at step 330 (FIG. 4B). If the pulse energy reaches a minimum available setting at decision step 320 prior to a sustained loss of capture being detected at step 315, then the first threshold setting $T_1$ is set equal to the minimum pulse energy at step 322. A second threshold setting $T_2$ needed to calculate the Wedensky Effect value is indeterminable since sustained loss of capture was not verified. This result is also logged to memory 94 at step 322.

If the first threshold setting $T_1$ is found to be greater than the minimum pulse energy setting, method 300 proceeds to step 335 to search for the threshold setting $T_2$. At step 335, the pulse energy is increased by increasing either the pulse amplitude or the pulse width.

Method 300 then proceeds to decision step 340, where it determines if sustained capture is verified at the increased stimulating pulse energy. Preferably, capture must be verified for a given number of consecutive stimulation cycles, for example 2 consecutive stimulation cycles. The pulse energy at which sustained capture first occurs is considered to be the second threshold setting $T_2$, and this setting is stored in memory 94 at step 350.

If sustained capture is not detected at step 340, the pulse energy setting is compared to the maximum available pulse energy setting at decision step 345. If the pulse energy has not reached the maximum setting available, the method 300 returns to step 335 to increase the pulse energy by one more step. Steps 335, 340 and 345 are repeated until the threshold requirement of decision step 340 is met.

If the maximum pulse energy is reached before sustained capture is detected at step 340, the second threshold setting $T_2$ is stored in memory 94 as being greater than the available energy settings at step 347. If sustained capture is verified at decision step 340, the method 300 considers the current pulse energy to be equal to the second threshold setting $T_2$, and stores this value in memory 94.

Having stored the values of the threshold settings $T_1$ and $T_2$, the method 300 restores the programmed stimulation parameters at step 355. The method 300 is thus completed and calls upon method 400 (FIG. 5) at termination step 360, to verify the reliability of the threshold settings $T_1$ and $T_2$.

Figure 5:
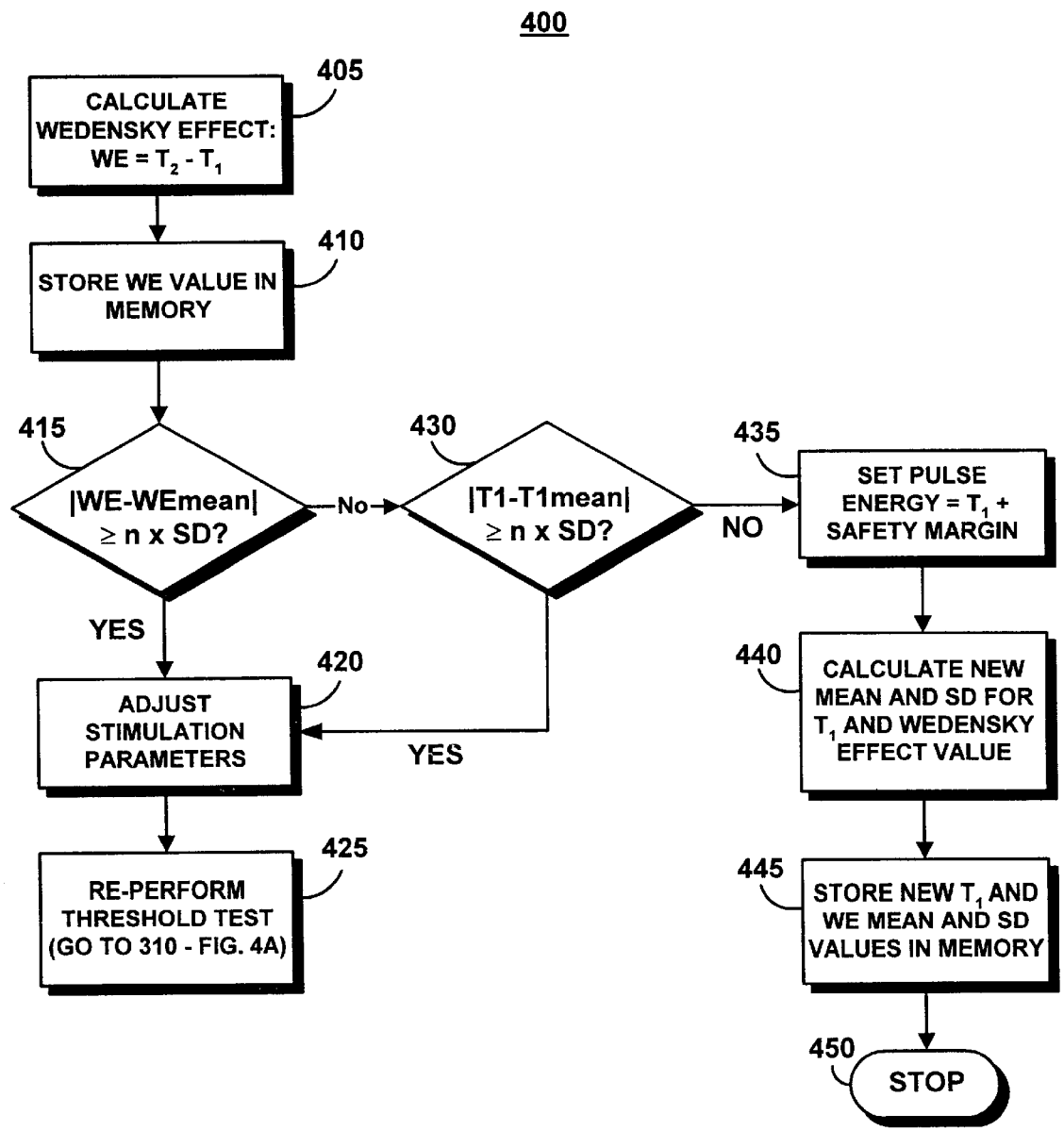
FIG. 5 is a flow chart describing an overview of the operation of one embodiment of the present invention in which the threshold test result as determined by the methods of FIGS. 3 and 4, is evaluated for possible influence of fusion.

FIG. 5 illustrates an overview of the operation and features implemented in one embodiment of the stimulation device 10 for testing if the first threshold setting $T_1$ is anomalous due to fusion activity during the threshold test method 300. Method 400 begins at step 405 by calculating the Wedensky Effect value (WE), which is the difference between the first threshold setting T1, and the second threshold setting $T_2$. This Wedensky Effect value is expected to remain stable over time, regardless of clinical state, implant duration or changes in the magnitude of the threshold value itself. The new Wedensky Effect (WE) value is stored in memory 94 at step 410.

At step 415, this new Wedensky Effect (WE) value is compared to an expected Wedensky Effect value. The expected Wedensky Effect value is preferably determined by calculating a mean Wedensky Effect value based on all previous threshold tests performed according to method 300. The new Wedensky Effect value should fall within a pre-defined range of the mean Wedensky Effect value, for example within one or more standard deviations of the mean Wedensky Effect value.

Hence, at decision step 415, the absolute value of the difference between the Wedensky Effect value (WE) and the mean Wedensky Effect value (WEmean) is compared to the value of n standard deviations (SD) where n is a predefined number, typically one to three. If the difference between the Wedensky Effect value (WE) and the mean Wedensky Effect value (WEmean) is greater than n standard deviations (SD) of the mean Wedensky Effect, then the threshold test results are suspected of being anomalous, possibly due to fusion.

Hence, at step 420 the stimulation parameters are adjusted such that the likelihood of fusion is minimized. For example, during threshold testing in the ventricle, the atrial to ventricular escape interval is decreased in an effort to ensure that the ventricular stimulation pulse will be delivered earlier than the intrinsic ventricular response. In single chamber stimulation applications, the base stimulation rate may be increased. After adjusting the stimulation parameters, a threshold test method 300 is performed again at step 425 to obtain new threshold results for the first threshold setting $T_1$ and the second threshold setting $T_2$.

If the Wedensky Effect value stored at step 410 is not significantly different than the expected mean Wedensky Effect value as determined at decision step 415, then the threshold test is presumed accurate. However, a situation may conceivably exist in which the Wedensky Effect value is approximately equal to the expected result yet fusion activity has affected both threshold settings $T_1$ and $T_2$. Therefore, at decision step 430, the first threshold setting $T_1$ is compared to an expected first threshold setting $T_1$ as an added confirmation of correct threshold test results.

The absolute value of the difference between the first threshold setting $T_1$ and the average of all previous threshold settings $T_1$ ($T_1$mean) is compared to a given number (n) of standard deviations (SD) of $T_1$ mean. The number of standard deviations (n) may be a fixed or programmable value and is typically one to three standard deviations.

If the first threshold setting $T_1$ is within the defined range (n standard deviations) over $T_1$ mean, then the first threshold setting $T_1$ is accepted as the new threshold value, and the stimulating pulse energy is adjusted to the new threshold setting $T_1$ plus some predefined safety margin at step 435. The safety margin may be, for example, one additional pulse amplitude setting or one additional pulse width setting.

At step 440, the mean values and standard deviations (SD) for the Wedensky Effect (WE) and threshold setting $T_1$ are re-calculated using the current threshold $T_1$ and $T_2$ results and all previous threshold test results. The new mean and standard deviation (SD) values are stored in memory 94 at step 445. Having verified that the threshold test is not likely to have been affected by fusion and having made the appropriate adjustment to the programmed pulse energy, method 400 is terminated at step 450.

If at decision step 430 the method 400 determines that the first threshold setting $T_1$ is not within the defined range over $T_1$ mean, then the threshold test results are suspected of being anomalous, possibly due to fusion, and the stimulation parameters are adjusted at step 420, as explained earlier, such that the likelihood of fusion is minimized.

Thus a method has been provided by which a threshold test is performed and the results analyzed in order to determine if fusion was likely to have caused an erroneous result. If fusion is suspected, the threshold test is repeated at new stimulation parameters expected to reduce the likelihood of fusion. In this way, a method of automatically and accurately determining stimulation threshold and appropriately adjusting stimulation energy is provided, thereby improving battery longevity and cardiac stimulating device performance.

What is claimed is:

1. A method of automatically performing a threshold test, comprising:

measuring a first threshold setting ($T_1$) by progressively decreasing a stimulation energy until capture is lost;

measuring a second threshold setting ($T_2$) by progressively increasing the stimulation energy until capture is verified;

calculating a difference between the first threshold setting ($T_1$) and the second threshold setting ($T_2$); and verifying the validity of the threshold test by monitoring a change in the difference between the first threshold setting ($T_1$) and the second threshold setting ($T_2$).

2. The method according to claim 1, wherein measuring the first threshold setting ($T_1$) includes starting with an initial supra-threshold stimulation energy setting and gradually decrementing the initial stimulation energy.

3. The method according to claim 2, wherein measuring the first threshold setting ($T_1$) includes setting the first threshold setting ($T_1$) as a stimulation energy at which capture is detected.

4. The method according to claim 1, wherein measuring the second threshold setting ($T_2$) includes starting with an initial sub-threshold stimulation energy setting and gradually increasing the initial stimulation energy.

5. The method according to claim 4, wherein measuring the second threshold setting ($T_2$) includes setting the second threshold setting ($T_2$) as a stimulation energy at which capture is regained.

6. The method according to claim 1, wherein verifying the validity of the threshold test includes comparing the difference between the first threshold setting ($T_1$) and the second threshold setting ($T_2$), to an expected Wedensky Effect value.

7. The method according to claim 6, further including calculating the expected Wedensky Effect value for a particular patient by calculating a mean Wedensky Effect based on previously performed threshold tests for the patient.

8. The method according to claim 1, wherein if the validity of the threshold test is not verified, adjusting stimulation parameters and repeating the threshold test based on adjusted stimulation parameters.

9. The method according to claim 1, wherein if the validity of the threshold test is verified, automatically adjusting the stimulation energy to a safely level above a threshold value.

10. A method of automatically determining the occurrence of fusion, comprising:

measuring a first threshold setting ($T_1$) by progressively decreasing stimulation energy until capture is lost;

measuring a second threshold setting ($T_2$) by progressively increasing the stimulation energy until capture is verified;

measuring a difference between the first threshold setting ($T_1$) and the second threshold setting ($T_2$); and verifying the occurrence of fusion by detecting a change in the difference between the first threshold setting ($T_1$) and the second threshold setting ($T_2$).

11. The method according to claim 10, wherein measuring the first threshold setting ($T_1$) includes starting with an initial supra-threshold stimulation energy setting at which capture is detected and gradually decrementing the initial stimulation energy.

12. The method according to claim 11, wherein measuring the second threshold setting ($T_2$) includes starting with an initial sub-threshold stimulation energy setting at which capture is regained, and gradually increasing the initial stimulation energy.

13. The method according to claim 11, wherein verifying the occurrence of fusion includes comparing the difference between the first threshold setting ($T_1$) and the second threshold setting ($T_2$), to an expected Wedensky Effect value.

14. The method according to claim 11, further includes calculating the expected Wedensky Effect value for a particular patient by calculating a mean Wedensky Effect based on previously performed threshold tests for the patient.

15. A cardiac stimulation device for automatically performing a threshold test, comprising:

an energy source that supplies stimulation energy;

a sensor connected to the energy source that measures a first threshold setting ($T_1$) by progressively decreasing a stimulation pulse energy until capture is lost, and that further measures a second threshold setting ($T_2$) by progressively increasing the stimulation energy until capture is verified; and a controller that calculates a difference between the first threshold setting ($T_1$) and the second threshold setting ($T_2$), and that verifies the validity of the threshold test by monitoring a change in the difference between the first threshold setting ($T_1$) and the second threshold setting ($T_2$).

16. The device according to claim 15, wherein the controller measures the first threshold setting ($T_1$) by starting with an initial supra-threshold stimulation energy setting at which capture is detected and then gradually decrementing the initial stimulation energy.

17. The device according to claim 15, wherein the controller measures the second threshold setting ($T_2$) by starting with an initial sub-threshold stimulation energy setting at which capture is regained, and then gradually increasing the initial stimulation energy.

18. The device according to claim 15, wherein the controller verifies the validity of the threshold test by comparing the difference between the first threshold setting ($T_1$) and the second threshold setting ($T_2$), to an expected Wedensky Effect value.

19. The device according to claim 15, wherein if the validity of the threshold test is not verified, the controller adjusts stimulation parameters and repeats the threshold test based on adjusted stimulation parameters; and wherein if the validity of the threshold test is verified, the controller automatically adjusts the stimulation energy to a safely level above a threshold value.

20. A cardiac stimulation device for automatically determining the occurrence of fusion, comprising:

an energy source that supplies stimulation energy;

a sensor, coupled to the energy source, that measures a first threshold setting ($T_1$) by progressively decreasing a stimulation energy until capture is lost, and that measures a second threshold setting ($T_2$) by progressively increasing the stimulation energy until capture is verified; and a controller that calculates a difference between the first threshold setting ($T_1$) and the second threshold setting ($T_2$), and that verifies the occurrence of fusion by detecting a change in the difference between the first threshold setting ($T_1$) and the second threshold setting ($T_2$).

21. The device according to claim 20, wherein the controller measures the first threshold setting ($T_1$) by starting with an initial supra-threshold stimulation energy setting at which capture is detected and then gradually decrementing the initial stimulation energy; and wherein the controller measures the second threshold setting ($T_2$) by starting with an initial sub-threshold stimulation energy setting at which capture is regained, and then gradually increasing the initial stimulation energy.

22. The device according to claim 21, wherein the controller verifies the validity of the threshold test by comparing the difference between the first threshold setting ($T_1$) and the second threshold setting ($T_2$), to an expected Wedensky Effect value;

wherein if the validity of the threshold test is not verified, the controller adjusts stimulation parameters and repeats the threshold test based on adjusted stimulation parameters; and wherein if the validity of the threshold test is verified, the controller automatically adjusts the stimulation energy to a safely level above a threshold value.

* * * * *